(12) United States Patent
Mortensen

(10) Patent No.: US 8,865,134 B2
(45) Date of Patent: Oct. 21, 2014

(54) CHEWING GUM

(75) Inventor: Nils Mortensen, Tonsberg (NO)

(73) Assignee: Med-Eq AS, Tonsberg (NO)

( * ) Notice: Subject to any disclaimer, the term of this patent is extended or adjusted under 35 U.S.C. 154(b) by 1300 days.

(21) Appl. No.: 12/083,451

(22) PCT Filed: Oct. 16, 2006

(86) PCT No.: PCT/GB2006/003834
§ 371 (c)(1),
(2), (4) Date: May 7, 2009

(87) PCT Pub. No.: WO2007/042835
PCT Pub. Date: Apr. 19, 2007

(65) Prior Publication Data
US 2010/0061939 A1  Mar. 11, 2010

(30) Foreign Application Priority Data

Oct. 14, 2005 (GB) .................................. 0520956.4

(51) Int. Cl.
| | | |
|---|---|---|
| *A61K 9/68* | (2006.01) | |
| *A61K 31/215* | (2006.01) | |
| *A61K 36/82* | (2006.01) | |
| *A23G 4/06* | (2006.01) | |
| *A23G 3/36* | (2006.01) | |
| *A23G 3/48* | (2006.01) | |

(52) U.S. Cl.
CPC .. *A23G 4/06* (2013.01); *A23G 3/36* (2013.01); *A23V 2002/00* (2013.01); *A23G 4/068* (2013.01); *A23G 3/48* (2013.01)
USPC .............................. 424/48; 514/506; 424/725

(58) Field of Classification Search
None
See application file for complete search history.

(56) References Cited

U.S. PATENT DOCUMENTS

| | | |
|---|---|---|
| 3,916,028 A | 10/1975 | Lee et al. |
| 3,924,017 A | 12/1975 | Lee et al. |
| 6,491,540 B1 | 12/2002 | Barreca |
| 2002/0127189 A1 | 9/2002 | Myers et al. |

FOREIGN PATENT DOCUMENTS

| | | |
|---|---|---|
| CA | 1026988 | 2/1978 |
| EP | 1 186 297 A2 | 3/2002 |
| EP | 1 559 421 A1 | 8/2005 |
| FR | 2734479 A1 * | 11/1996 |
| JP | 2003034636 | 2/2003 |
| WO | WO 95/00038 A1 | 1/1995 |
| WO | WO 02/100192 A1 | 12/2002 |
| WO | WO 2005/067952 A1 | 7/2005 |

OTHER PUBLICATIONS

Johnston et al. Coffee acutely modifies gastrointestinal hormone secretion and glucose tolerance in humans: glycemic effects of chlorogenic acid and caffeine. Am J Clin Nutr 2003;78:728-33.*
Suzuki et al. Green coffee bean extract and its metabolites have a hypotensive effect in spontaneously hypertensive rats. Hypertens. Res. 2002;25:99-107.*
Bertrand et al. Impact of the *Coffea canephora* gene introgression on beverage quality of *C. arabica*. Theor Appl Genet (2003) 107:387-394.*
Lee et al. Inhibition of DNA methylation by caffeic acid and chlorogenic acid, two common catechol-containing coffee polyphenols. Carcinogenesis 2006;27(2):269-277.*
Kothari, et al., "Coffee, Chlorogenic Acid, and Cholesterol," British Medical Journal, vol. 294, Feb. 21, 1987, pp. 512.
Thom, E. 2007 "The effect of chlorogenic acid enriched coffee on glucose absorption in healthy volunteers and its effect on body mass when used long-term in overweight and obese people" *J Int Med Res* 35: 900-908.
Bingham, S. et al. 1982 "The diet of individuals: a study of a randomly-chosen cross section of British adults in a Cambridgeshire village" *Br J Nutr* 45: 23-35.

* cited by examiner

*Primary Examiner* — Daniel Sullivan
*Assistant Examiner* — Peter Anthopolos
(74) *Attorney, Agent, or Firm* — Knobbe, Martens, Olson & Bear, LLP

(57) ABSTRACT

Chewing gum comprising an extract from coffee enriched in at least one ester formed between a trans-cinnamic acid and quinic acid wherein the amount of said at least one ester in the gum is 0.1 to 50 wt %.

4 Claims, No Drawings

CHEWING GUM

This application is the U.S. National Phase of International Application No. PCT/GB2006/003834, filed Oct. 16, 2006, which claims the benefit of British Application No. 0520956.4, filed Oct. 14, 2005.

This invention relates to chewing gum, more particularly to a chewing gum containing at least one ester of quinic acid and a trans-cinnamic acid, such as chlorogenic acid, which can aid weight loss.

Obesity is a growing problem in the Western World. Whilst many factors contribute to this problem, the main cause is an excess of sugar in the diet. The consequences of obesity are well documented and range from higher incidence of cancer to increased risk of diabetes.

Methods of treating obesity are also well known. Traditional methods such as calorie controlled diets and physical exercise programmes can be effective but individuals rarely adhere to the regime and often put back on any weight loss achieved when they finish their diet. Science has therefore been searching for ways in which weight loss can be achieved without recourse to strict dietary control and exercise.

"Chlorogenic acids" are a family of esters formed between trans-cinnamic acids and quinic acid. The commonest individual member of the "chlorogenic acids" is formed between caffeic acid and quinic acid and has the trivial name chlorogenic acid. Chlorogenic acid is a phenolic natural product isolated from the leaves and fruits of dicotyledonous plants, including the coffee bean. Structurally, chlorogenic acid is the ester of caffeic acid with the 3-hydroxyl group of quinic acid and its structure is shown below.

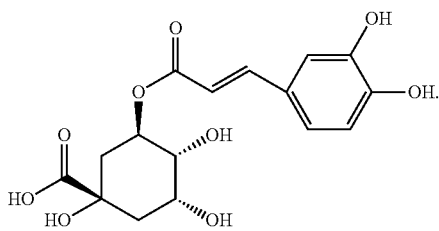 [SMILES: O=C(/C=C/c1ccc(O)c(O)c1)O[C@@H]1C[C@](O)(C(=O)O)C[C@@H](O)[C@H]1O]

In research on humans, chlorogenic acid has been shown to reduce the amount of carbohydrates absorbed. Furthermore, animal research using isolated chlorogenic acid demonstrated that this compound has the ability to reduce the amount of glucose that can be created from metabolism of carbohydrates and proteins. It has been realised therefore that chlorogenic acid offers potential benefit in that when the body is unable to derive energy from these sources, it may draw upon stored sources of energy (such as body fat) to help meet energy needs. It has been proposed therefore to use coffee bean extracts containing chlorogenic acid in dieting tablets. A number of such products are on the market, e.g. Xenadrine Carbo-Curb.

The present inventors have been investigating alternative dieting products other than the conventional pill/tablet/capsule. They have surprisingly found that chewing gum containing at least one ester of trans-cinnamic acid and quinic acid (from hereon termed the ester) is of still further benefit as a diet aid. By putting the ester in a chewable gum product, the ester is released slowly over a period of time whilst the gum is chewed. In effect therefore, the gum acts like a sustained release formulation preventing carbohydrate metabolism and absorption for a prolonged period. Moreover, it has surprisingly been found that the ester, e.g. chlorogenic acid, blocks the amylase enzyme. Amylase enzyme is present in saliva and in the gut and by chewing the gum of the invention amylase can be inhibited in the mouth and in the gut. Thus, as the ester is released by chewing, the gum prevents degradation of carbohydrates into glucose in the oral cavity by inhibiting amylase. Moreover, any salivary amylase which is swallowed can already be inhibited by the ester preventing it from having an effect during digestion. Furthermore, as the gum releases ester which is swallowed during the natural chewing process, the ester can go on to inhibit intestinally released amylase too. Thus, the use of the ester in chewing gum not only prevents carbohydrate metabolism in the mouth but also carbohydrate metabolism during digestion.

Thus, viewed from one aspect the invention provides chewing gum comprising an extract from coffee enriched in at least one ester formed between a trans-cinnamic acid and quinic acid, e.g. chlorogenic acid, wherein the amount of said at least one ester in the chewing gum is 0.1 to 50 wt %.

Viewed from another aspect the invention provides a method of weight loss, either clinical or cosmetic, comprising chewing the gum as hereinbefore described Viewed from another aspect the invention provides use of an extract of coffee enriched in at least one ester formed between a trans-cinnamic acid and quinic acid in the manufacture of chewing gum for the treatment of obesity wherein the amount of said at least one ester in the chewing gum is 0.1 to 50 wt %.

The term "chewing gum" is intended to cover well-known variations such as bubble gum or chewable tablets (i.e. tablets designed to be chewed as opposed to swallowed). Chewing gum is typically a flavoured gum product which is chewed for a prolonged period and then spat out rather than swallowed. The inventive concept stems from the slow release of the ester, e.g. chlorogenic acid, through chewing and its ability to inhibit amylase, e.g. salivary amylase. This effect will be observed for any chewable product such as a chewing gum. A typical diet tablet, however, will not act as a slow release composition or act to inhibit salivary amylase since the pill is swallowed without spending significant time in the oral cavity.

The chewing gum composition contains at least one ester formed between a trans-cinnamic acid and quinic acid. The chewing gum may contain a mixture of such esters or a single ester, e.g. chlorogenic acid. Preferably, the composition will contain a mixture of trans-cinnamic acid and quinic acid esters. These esters are often generically referred to as "chlorogenic acids" although chlorogenic acid is itself a specific compound as depicted above.

The at least one ester, preferably mixture of esters, is present in an extract from coffee in which the ester content has been enriched. By enriched is meant that the ester content of the extract has been concentrated or added to such that it is greater than that of the natural coffee extract, e.g. greater than that obtained directly from the coffee bean. The natural extract typically contains from 2 to 8 wt % esters. Thus, the extract from coffee used in the invention naturally contains at least one ester of transcinnamic acid and quinic acid but the content thereof has been artificially enriched.

Quinic acid is a compound of formula

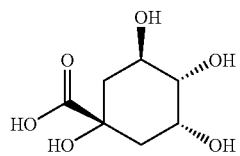 [SMILES: O=C(O)[C@]1(O)C[C@@H](O)[C@@H](O)[C@H](O)C1]

The ester with the trans-cinnamic acid can form from any of the hydroxyl groups thereof although preferably the ester linkage forms from the 3-position or 5-position of the cyclohexyl ring (the 1-position carries the carboxyl group).

Trans-cinnamic acids of use in forming the esters of the invention include those of formula (I)

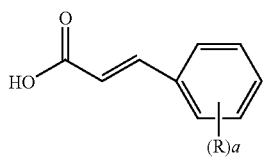

(wherein R is hydroxyl, $C_{1-10}$-alkyl (e.g. methyl, ethyl, isopropyl or tertbutyl), $C_{1-10}$-alkoxy (e.g. methoxy), halo (e.g. chloro), amino (e.g. $NH_2$ or $N(C_{1-6}$-alkyl$)_2$, or thiol; and a is 0 to 5. The cis isomer thereof could also be employed.

Preferably a is 0 or 2. R is preferably hydroxyl. If present, R groups are preferably positioned on the 2 and/or 3-positions of the ring. Especially preferably, the trans-cinnamic acid is caffeic acid

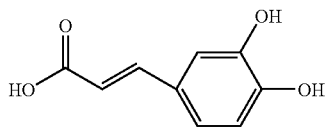 [SMILES: O=C(O)/C=C/c1ccc(O)c(O)c1]

Most preferably the ester is chlorogenic acid as depicted above. Chlorogenic acid is also often named as 5-caffeoyl-quinic acid.

Since the ester of the invention comprises a carboxyl group, it can also be present in salt form although preferably it is used in its acid form.

The amount of at least one ester, e.g. chlorogenic acid, in the chewing gum of the invention can vary but is preferably between 0.1 to 50 wt %, e.g. 0.1 to 30 wt %, preferably 0.1 to 20 wt %, e.g. 0.5 to 10 wt %, more preferably 1 to 5 wt %.

The at least one ester itself is present in coffee beans. The at least one ester is thus introduced into the chewing gum formulation as an extract from coffee, preferably green coffee, in which the ester content has been enriched, e.g. such that the extract contains a minimum of approximately 15 wt %, preferably at least 20 wt %, more preferably at least 25 wt %, especially at least 30 wt % ester, ideally at least 40 wt % ester, most especially 45 wt % ester(s).

Preferably, the ester may be introduced into the chewing gum formulation as part of Meditol™. Meditol™ (also known as Svetol™) contains a minimum of approximately 45 wt % esters and is an extract from green coffee in which the ester content has been enriched.

The amount of the specific ester chlorogenic acid in the formulation may be 5 to 25 wt % of the enriched extract, preferably 8 to 20 wt %, e.g. about 10%.

The coffee extract, in addition to the ester portion may contain polyphenols. The amount of such polyphenols may be 5 to 25 wt % of the enriched extract, preferably 8 to 20 wt %, e.g. about 10%.

Preferably the coffee extract is decaffeinated (i.e. either the extract is decaffeinated or the coffee from which the extract is obtained is decaffeinated). By decaffeinated means the caffeine content of the enriched extract is less than 2 wt %, preferably less than 1 wt %, especially less than 0.5 wt %, most preferably free of caffeine.

The extract may be obtained from any coffee, in particular, green coffee, however C. arabica and C. canephora are particularly preferred. The extract is preferably obtained from beans of the species Coffea canephora robusta P. and is preferably the hydroalcoholic extract; e.g. comprising: 10 wt % or more polyphenols, 45 wt % or more total esters, 10 wt % or more chlorogenic acid and 2 wt % or less caffeine.

The chewing gum can contain other conventional components of a chewing gum such as sweeteners (e.g. xylitol, sorbitol, malitol), colourings, flavourings (peppermint, menthol etc), lecithin, as well as the gum base. It will be appreciated that as this product is designed to encourage weight loss, sugars should preferably not be used in the chewing gum's manufacture.

Sweeteners can form 20 to 70% wt of the gum. The gum base typically forms between 15 and 40 wt % of the product. All other components are added in minor amounts, e.g. less than 5 wt %.

It is a further benefit of the invention that no further antioxidant needs to be added to the gum since the at least one ester also acts as an antioxidant.

The chewing gums of the invention can be manufactured using known procedures. The at least one ester, e.g. chlorogenic acid can therefore be introduced into any existing chewing gum manufacturing process without difficulty.

The chewing gums of the invention can be used to aid weight loss in individuals who may be slightly overweight to those that might be clinically obese. Weight loss in those individuals only slightly overweight (e.g. those with a body mass index of 25 to 30) may be regarded as essentially cosmetic.

Whilst the invention has been described in relation to chewing gum, it will be appreciated that the potential for sustained release of chlorogenic acid with associated saliva amylase inhibition exists with other products which remain in the oral cavity for a prolonged period of time. Such products could include lozenges and other suckable, preferably hard confectionary (boiled sweets, rock etc). It will of course be necessary to formulate such products with minimal or preferably without sugar to maximise any weight loss effects.

Thus, viewed from a further aspect the invention provides a preferably sugar free confectionary composition comprising an extract from coffee enriched in at least one ester formed between a trans-cinnamic acid and quinic acid wherein the amount of said at least on ester in the composition is 0.1 to 50 wt %, adapted to remain in the oral cavity for a prolonged period, e.g. at least 5, preferably at least 10 minutes.

By confectionary adapted to remain in the oral cavity for a prolonged period means that the composition is in the form of a suckable lozenge or the like and is designed to be sucked by the consumer. The product is one which does not quickly dissolve in the oral cavity, so is preferably hard. This means that once the product has been placed in the oral cavity it does not rapidly dissolve or is not swallowed; rather it is sucked and will remain suckable over a prolonged period, e.g. at least 10 minutes. This ensures that release of the at least one ester takes place over a period of time.

As the product requires prolonged sucking in the mouth to slowly dissolve in the oral cavity the composition does not cover a tablet which is designed to be swallowed immediately rather than sucked or a chocolate bar which is chewed and swallowed. The term covers lozenges, lollipops, rock, boiled sweets and the like. Ideally, the confectionary may be a mint.

Such a product can be formulated readily by the skilled man based on existing technology using flavourings, colourings, gum bases etc well known in the art. To avoid the use of sugar, sweeteners such as xylitol or sorbitol can be employed. The amount of ester, e.g. chlorogenic acid, present may range from 0.1 to 20 wt %, preferably 1 to 10% wt, e.g. 2 to 5 wt % of the composition.

The invention will now be described with reference to the following non-limiting examples.

EXAMPLE 1

| Sugar free Chewing Gum | |
|---|---|
| Ingredients | Amount (mg) |
| Xylitol | 390.0 |
| Gum base | 350.7 |
| Maltitol | 312.0 |
| Sorbitol | 104.0 |
| Meditol ™ powder | 100.0* |
| Flavourings (peppermint, menthol) | 24.8 |
| Lecithin | 6.0 |
| Glycerol | 6.0 |
| Acesulframe K | 2.5 |
| Gum Arabic | 1.9 |
| Colour E171 (TiO2) | 1.8 |
| Glazing agent: camauba wax, beeswax, shellac | 0.3 |
| Chromate | 0.07 |

*minimum 45 wt % ester

EXAMPLE 2

Studies were carried out using Meditol™, an extract of green coffee where the content of ester has been enriched to 45% wt. 200 mg capsules were employed thus each capsule contained 90 mg of Meditol™.

The study was carried out as an open study with 15 healthy volunteers. Each subject was given three Meditol™ capsules a day, one in the morning, one at lunch and one in the evening. No other dietary requirement were specified and no stipulations were made on physical activity during the test period.

The glucose loading part of the study was carried out after 8 hours fasting. Each subject received 18 jelly beans after fasting and blood glucose levels were measured prior to and 1 hour after jelly bean ingestion.

The blood sugar levels of the 15 subjects were also measured when not on the Meditol™ regime.

A comparison of blood sugar levels revealed that glucose level is reduced significantly after a single dose of Meditol™. The reduction in absorption is approximately 20% when the glucose values are compared one hour after ingestion with or without Meditol™. The majority of patients experienced a positive effect.

Results

| Subject | Baseline Pre-load | Baseline 1 hr post load | Meditol Baseline | Meditol 1 hr post load |
|---|---|---|---|---|
| 1 | 106 | 164 | 80 | 104 |
| 2 | 136 | 244 | 118 | 210 |
| 3 | 94 | 117 | 94 | 142 |
| 4 | 115 | 171 | 93 | 152 |
| 5 | 106 | 145 | 104 | 131 |
| 6 | 96 | 123 | 87 | 68 |
| 7 | 108 | 145 | 107 | 154 |
| 8 | 80 | 102 | 85 | 93 |
| 9 | 106 | 164 | 99 | 154 |
| 10 | 119 | 176 | 111 | 145 |
| 11 | 103 | 156 | 107 | 129 |
| 12 | 86 | 113 | 128 | 150 |
| 13 | 102 | 122 | 79 | 115 |
| 14 | 90 | 163 | 96 | 102 |

(numbers represent serum glucose levels)

EXAMPLE 3

| Sugar free Mint | |
|---|---|
| Ingredients | Amount (mg) |
| Xylitol | 565 |
| Calcium carbonate | 10 |
| Magnesium Stearate | 9.0 |
| Arom | 8.0 |
| Meditol ™ powder | 50.0* |
| Gum Arabic | 7.0 |
| Glazing agent | 1.0 |

*minimum 45 wt % ester

The invention claimed is:

1. A unit portion of chewing gum comprising:
   a gum base;
   a sweetener;
   a flavoring; and
   5-caffeoylquinic acid (5-CQA); and
   wherein the concentration of 5-CQA relative to the unit portion of chewing gum is greater than or equal to 0.1 weight percent and less than or equal to 10 weight percent.

2. The unit portion of chewing gum of claim 1, wherein the concentration of 5-CQA relative to the unit portion of chewing gum is greater than or equal to 0.5 weight percent and less than or equal to 10 weight percent.

3. The unit portion of chewing gum of claim 1, wherein the concentration of 5-CQA relative to the unit portion of chewing gum is greater than or equal to 1 weight percent and less than or equal to 10 weight percent.

4. The unit portion of chewing gum of claim 1, wherein the concentration of 5-CQA relative to the unit portion of chewing gum is greater than or equal to 1 weight percent and less than or equal to 5 weight percent.

* * * * *